United States Patent [19]

Price et al.

[11] 4,410,506
[45] Oct. 18, 1983

[54] IMMUNOASSAY FOR VITAMIN K-DEPENDENT BONE PROTEIN

[75] Inventors: Paul A. Price, San Diego, Calif.; Satoru K. Nishimoto, Bristol, Conn.

[73] Assignee: The Regents of the University of California, Berkeley, Calif.

[21] Appl. No.: 246,972

[22] Filed: Mar. 24, 1981

[51] Int. Cl.$^3$ .................... G01N 33/56; G01N 33/58; G01N 33/60
[52] U.S. Cl. .................... 436/542; 424/85; 435/7; 436/545; 436/546; 436/547; 436/800; 436/804; 436/811
[58] Field of Search ............ 424/1, 12, 85, 88; 23/230 B; 435/7; 260/112 R, 112 B

[56]     References Cited
U.S. PATENT DOCUMENTS 3,852,157  12/1974  Rubenstein et al. .............. 424/12 X
3,966,556   6/1976  Rubenstein et al. .................. 195/63

OTHER PUBLICATIONS

Hauschka et al., Proc. Natl. Acad. Sci. USA, 72:3925–3929 (1975).
Lian et al., Fed. Proc., 37:2615–2620 (1978).
Price et al., Proc. Natl. Acad. Sci. USA, 77:2234–2238 (1980).
Poser et al., J. Biol. Chem., 255: 8685–8691 (1980).
Price et al., J. Biol. Chem., 256: 3781–3784 (1981).
Price et al., Biochem. Biophys. Res. Comm., 99: 928–935 (1981).

Primary Examiner—Christine M. Nucker
Attorney, Agent, or Firm—Bertram I. Rowland

[57]     ABSTRACT

Immunoassay and compositions therefore for detection of human vitamin K-dependent bone protein. Heterologous labeled vitamin K-dependent protein or antigenic fragment thereof is employed with antibodies to the protein in an assay for the protein in various physiological fluids for bone extracts. The assay may be used in the diagnosis of bone diseases, by itself or in conjunction with an alkaline phosphatase assay.

14 Claims, No Drawings

IMMUNOASSAY FOR VITAMIN K-DEPENDENT BONE PROTEIN

The invention described herein was made in the course of work under a grant or award from the Department of Health and Human Services.

BACKGROUND OF THE INVENTION

1. Field of the Invention

The assessment of bone metabolism and bone disease remains a difficult problem in clinical medicine. The measurements of alkaline phosphatase in blood and hydroxyproline in urine have been the most widely used biochemical tests for this purpose. Although these measurements are of considerable clinical value, each has its limitations. Alkaline phosphatase is not a specific reflection of bone function, because its concentration in blood is also contributed to by the liver, gastrointestinal tract, placenta, certain tumors, and perhaps other sources. Hydroxyproline is similarly not specific for bone because it can be influenced by diet and nonosseous as well as osseous collagen.

It would therefore be of substantial value to have an assay which could be used in the specific diagnosis of bone related diseases, either independently or as a confirmation of other diagnostic factors.

2. Description of the Prior Art

An abstract of a paper by Price et al. was published in June, 1979, for the meeting of the American Society For Bone And Mineral Research. Price and Nishimoto, Proc. Natl. Acad. Sci. USA 77, 2234-2238 (1980) and Price et al., J. Clin. Invest. 66, 878-883 (1980) both describe the subject invention. The references cited in the aforementioned references should also be noted.

SUMMARY OF THE INVENTION

Labeled xenogeneic vitamin K-dependent bone protein is employed as a reagent in immunoassays for determining the level of the aforementioned protein in physiological fluids and bone extracts. The bone protein level in the physiological fluid can be related to disease diagnosis.

DESCRIPTION OF THE SPECIFIC EMBODIMENTS

Immunoassays and reagents therefore are provided, where cross-reacting heterologous vitamin K-dependent bone protein or antigenic fragment thereof is employed as a labeled reagent in immunoassays and for stimulating the formation of antibodies to the bone protein for use in the determination of the level of the bone protein in human bone or human physiological fluids. The method can employ a wide variety of labels and techniques for the determination of polypeptides.

In preparing the reagents of the subject immunoassays, vitamin K-dependent bone protein (hereinafter referred to as BGP) is obtained from other than a human source which provides BGP which cross-reacts with human BGP. Specifically, bovine, particularly calf, BGP or antigenic fragment thereof can be employed for the preparation of the reagents for use in the immunoassay. Fragments will normally include at least 20 amino acids from the carboxyl terminus, the total polypeptide having 49 amino acids.

The BGP which is employed can be obtained by demineralization of the appropriate mammalian species other than human and purified by gel filtration and gradient elution. In this way, purified non-human BGP can be obtained which provides a single band on electrophoresis in 20% acrylamide gels and a single band on isoelectric focusing gels in accordance with known methods (Nishimoto and Price (1979) J. Biol. Chem. 254, 437-441).

Based on protease digestion, the amino acids from 1 to 28, numbering from the amino terminus do not appear to be required for antigenicity. Therefore, an oligopeptide of at least 20 amino acids from the carboxy terminus of BGP can be used, instead of the intact BGP.

It is further found, that the BGP varies sufficiently in a number of species, that BGP from a non-human source which cross-reacts with a human source can be used as an antigen in a variety of domestic animals for production of antisera. Furthermore, in accordance with known techniques, various small domestic animals e.g. mice, can be immunized with the non-human cross-reacting BGP to provide for production of monoclonal antibodies, specific for human and the cross-reacting BGP.

Depending upon the nature of the particular immunoassay, various labels may be employed. The chosen label will be required to provide for sensitivity in the range of interest of the BGP for the particular assay.

Among labels which have found use in immunoassays are radionuclides, enzymes, fluorescers, magnetic particles, stable free radicals, etc. Methods employing these various labels may be found in U.S. Pat. Nos. Re 29169; Re 29,955; U.S. Pat. Nos. 3,654,090; 3,690,834; 3,817,837; 3,867,517; 3,935,074; 3,975,511; 3,996,345; and 4,020,151. These references are only illustrative of the wide variety of techniques to which the subject reagents may be applied.

Illustrative fluorescers include fluorescein, dansyl, rhodamines, acridines, etc. Illustrative enzymes include horse radish peroxidase, amylase, lipozyme, glucose-6-phosphate dehydrogenase, malate dehydrogenase, $\beta$-galactosidase, etc.

The manner in which the BGP or fragment thereof may be conjugated to or labeled with the various labels has been amply described in the literature for each of the labels. With a radionuclide, various radionuclides may be employed, preferably a radioactive iodine, more particularly $^{125}I$. The manner of labeling with iodine is well known. Where the label is other than another polypeptide, normally the label will be functionalized with a carboxylic acid or derivative thereof or aldehyde for conjugation to BGP, resulting in amide bonds or methyleneamine links by reductive amination. With other polypeptides, various cross linking agents may be employed, such as glutaraldehyde, p-maleimidobenzoic acid, 6-maleimidocaproic acid or the like.

Antibodies may be prepared in conventional ways, by injecting the BGP with an appropriate carrier into a host in which the BGP is an immunogen. It is found that bovine, particularly calf, BGP is immunogenic in the order Lagomorpha e.g. rabbit and order Rodentia, e.g. rat. By an appropriate program of sequential injections with immunogen, antisera to BGP of high titer and specificity can be obtained. In addition, as desired, spleens or peripheral blood cells may be taken from the immunized animal and used in accordance with known technology to prepare monoclonal antibodies to BGP. (Kohler and Milstein (1975) Nature 356, 495-7; (1976) Euro. J. Immunol. 6: 511-519). The monoclonal antibodies are obtained by fusing the lymphocytes with an immortalized myeloma line which is HAT sensitive, followed by growing the fused cells in a HAT-containing medium and then cloning and selecting cells providing antibodies to BGP.

The assays will be carried out in accordance with known techniques depending upon the nature of the label. Various techniques involve competition between labeled BGP and BGP analyte in a sample suspected of containing BGP. Various samples of interest in which BGP may be assayed include serum, plasma, urine, cerebrospinal fluid, amniotic fluid and saliva. In addition to the aforementioned biological fluids, extracts, particularly acid extracts of human tissues, such as bone, teeth, and pathological calcifications (ectopic calcifications and hardened arteries) may also be of interest.

In performing the assay, the sample containing the analyte, the labeled BGP or fragment thereof, and antibodies to BGP (anti-BGP) will be brought together in an aqueous buffered medium, normally of a pH in the range of about 6 to 9, and the partitioning of the labeled BGP between being unbound and bound to the antibody determined. Depending upon the nature of the assay, a separation ("heterogeneous") or no separation ("homogeneous") may be involved. This will depend upon whether the binding of antibody to the labeled reagent affects the signal resulting from the reagent. While radionuclides require a separation, enzyme and fluorescer labels may or may not require a separation. The order of addition may vary, where all the materials are brought together simultaneously or the sample is brought together with the anti-BGP, followed by the addition of the labeled BGP or BGP fragment. Incubation steps may be involved between the various additions, usually being not less than five minutes nor more than about 24 hours. Either a rate or equilibrium measurement may be involved. The bound labeled BGP may then be separated from the unbound BGP where a heterogeneous assay is involved, and the signal measured from the label in accordance with the nature of the label. Where no separation is required, the signal will be determined directly from the assay medium.

Depending on the nature of the radiation to be measured, gamma counters, scintillation counters, spectrophotometers, fluorimeters, etc. may be employed.

The following examples are offered by way of illustration and not by way of limitation.

MATERIALS AND METHODS

Preparation of BGP's.

BGP was purified from the proteins released by demineralization of calf, rat, rabbit, human, and swordfish bone by gel filtration over Sephadex G-100 and subsequent gradient elution from DEAE-Sephadex A-25 as described (Price et al. (1976) PNAS USA 73, 1447-1451; Price et al. (1976) ibid 3374-3375; Price and Williamson (1979) in Vitamin K Metabolism and Vitamin K-dependent Proteins, ed. Suttie, J. W. (Univ. Park Press, Baltimore, Md.) pp. 219-226). An additional affinity chromatography step with purified rabbit antibody against calf BGP as the specific adsorbent was used in the purification of the human protein. Partial sequence analysis of purified human BGP gave tyrosine and leucine as the first two NH$_2$-terminal amino acids, the same NH$_2$-terminal amino acids found in calf BGP. The DEAE-Sephadex-purified calf BGP used for immunizations, iodinations, and standards gave a single band on electrophoresis in 20% acrylamide gels and a single band on isoelectric focusing gels by using described methods. (Nishimoto and Price (1979) J. Biol. Chem. 254, 437-441). Tryptic peptides corresponding to residues 1-19, 20-43, and 45-49 and the carboxypeptidase Y digestion product corresponding to residues 1-40 were prepared as described in Price et al., supra.

Preparation of Radioiodinated Calf BGP.

Purified calf BGP was labeled with $^{125}$I($4 \times 10^{18}$ cpm per mol of I, Amersham) by the solid state lactoperoxidase method by incubating 10 $\mu$g of BGP with 1 mCi of $^{125}$I (1 Ci = $3.7 \times 10^{10}$ becquerels) (David and Rersfeld (1974) Biochemistry 13, 1014-1021). The labeled BGP was separated from unincorporated $^{125}$I by gel filtration on a Sephadex G-25 column equilibrated with assay diluent (0.14 M NaCl/0.01 M phosphate/25 mM EDTA/0.1% gelatin/0.1% Tween-20 at pH 7.4).

Preparation of Antibodies.

The rabbits were immunized by monthly multiple site intradermal injection of purified calf BGP adsorbed to polyvinyl pyrrolidone (PVP-40) (Worobec et al. (1972) Immunochemistry 9, 229-238). Each injection was made with 0.5-10 mg of purified BGP emulsified in either complete (initial challenge) or incomplete Freund's adjuvant. Serum samples were withdrawn at regular intervals and tested for the titer of antibody to BGP by radioimmunoassay.

Radioimmunoassay.

All assays contained (in order of addition) 0.2 ml of assay diluent, either a known amount of unlabeled BGP in 0.1 ml of assay diluent or 0.1 ml of heparinized plasma sample, 0.125 $\mu$l of antiserum R397(final 1:4000 dilution) and 2.5 $\mu$l of normal rabbit serum in 0.1 ml of assay diluent, and 15,000 cpm of $^{125}$I-labeled BGP in 0.1 ml of assay diluent. For the equilibrium radioimmunoassay all components were combined and incubated for 20 hr at 25° C. For the non-equilibrium assay all components except $^{125}$I-labeled BGP were combined and incubated for 24 hr at 4° C. followed by addition of $^{125}$I-labeled BGP and a second 24-hr incubation at 4° C. Assays were terminated by precipitation of rabbit antibody with the addition of 1.9 units of goat antiserum to rabbit $\gamma$-globulin (Calbiochem, lot 860217) in 0.1 ml of assay diluent. After 1.5 hr at 25° C. reaction mixtures were centrifuged to sediment $^{125}$I-labeled BGP bound to rabbit antibody and the supernatant was discarded. Background $^{125}$I label that nonspecifically adhered to the precipitate or to the glass reaction tube was measured by incubating $^{125}$I-labeled BGP and normal rabbit serum without specific antiserum followed by the usual second antibody precipitation. Total and antibody-bound $^{125}$I-labeled BGP were determined by assay in a Nuclear Chicago gamma counter for times sufficient to achieve a 2% counting accuracy. The fraction of $^{125}$I-labeled BGP bound to antiserum, B, is defined as cpm in precipitate minus cpm in background divided by total cpm in assay; $B_O$ is the value of B when no unlabeled BGP is present. The $B_O$ values for each radioimmunoassay reported here are the average of nine independent determinations and the B values for all standards and unknowns are the average of three independent measurements.

Preparations of purified BGP from human, rat, rabbit, and swordfish bone were tested for radioimmunoassay cross-reactivity by measuring the effect of different amounts of the purified BGP preparations on binding of $^{125}$I-labeled calf BGP to antibody. Serum samples from rat, rabbit, and calf and human plasma samples were also tested for cross-reactivity in this way, and the nonspecific effect of plasma or serum samples on the radioimmunoassay was tested by adding known quantities of calf BGP to the samples. The apparent molecular weight of BGP in circulation was investigated by comparing the Sephadex G-100 elution position of heparinized human plasma and calf serum BGP as determined by radioimmunoassay with the elution position of purified calf or human BGP. In order to test the stability of plasma BGP, heparinized human plasma samples were assayed after incubation at 25° C. for 24 hr or at 4° C. for 72 hr, after repeated freeze-thawing, and after lyophilization. Human plasma and serum samples from the same subjects were also compared.

RESULTS

Preparation of Radioiodinated Calf BGP.

Iodination of pure calf BGP by the lactoperoxidase method gives an $^{125}$I-labeled protein with a specific radioactivity of 40–50 mCi per mg. Over 90% of this labeled protein binds to an excess (1:100 dilution) of antibody raised to purified calf BGP. Labeled BGP is stable when stored in assay diluent, retaining over 90% of its initial immunologic activity after 8 weeks at $-20°$ C. Repeated freezing and thawing has no effect on the immunologic activity of iodinated BGP.

Preparation of Antisera to Calf BGP.

All ten rabbits produced antibody to BGP within 4 weeks after the initial injection, whereas no antibody could be detected in sera from 10 control rabbits. The antiserum (batch R397) that bound 20% of the iodinated BGP at the highest dilution was used for all radioimmunoassays reported here.

Radioimmunoassay for BGP.

Rabbit antiserum to calf BGP was used in both equilibrium and non-equilibrium radio-immunoassays. Standard curves can be constructed for both assays by plotting the relative fraction of labeled BGP bound to antibody ($B/B_O$) against increasing amounts of unlabeled calf BGP. The non-equilibrium assay is somewhat more sensitive than the equilibrium assay, with a detection limit of 0.1 ng compared with 0.3 ng. However, the more rapid equilibrium assay has an adequate sensitivity and was used in all further experiments. The intraassay variation of the equilibrium radioimmunoassay is typically less than 10%. Interassay variation was evaluated by repeated measurement of calf and human serum standards and was less than 15% in 20 assays performed over a 6-month period.

The radioimmunoassay for calf BGP was tested for cross-reactivity with BGP purified from human, rat, rabbit, and swordfish bone. Human BGP completely displaced labeled calf BGP from antibody and the standard curve generated by dilutions of human BGP parallels the calf BGP standard curve. On nanogram of human BGP is equivalent to 1 ng of calf BGP in the radioimmunoassay and so dilutions of purified calf BGP were used as standards in radioimmunoassay for the calf and human proteins. BGP's from rat, rabbit, and swordfish bone did not displace labeled calf BGP from antibody, even at 1 µg of added protein. Thus, the radioimmunoassay for the calf BGP cross-reacts with the human BGP but not with BGP of other species tested.

Location of the Antigenic Site.

The location of the region of calf BGP recognized by the rabbit antibody was determined with peptides derived from enzymic digests of BGP and with chemically modified forms of BGP. Specific thermal decarboxylation of γ-carboxyglutamate to glutamate (Doser and Price (1979) J. Biol. Chem. 254, 431–436) has no effect on antigenicity. Thus, the unique vitamin K-dependent region of BGP is not part of the antigenic determinant. This result also shows that the radioimmunoassay detects non-γ-carboxylated BGP such as might be present in coumadin-treated animals. Reduction and carboxamidomethylation of the single disulfide bond had no effect on antigenicity, which suggest that antigenicity is not dependent on the native conformation of BGP. Because the three γ-carboxyglutamate residues are at positions 17, 21, and 24 and the disulfide bond joins half-cystine residues at positions 23 and 28, the region between 17 and 28 in the 49-residue sequence is probably not involved in antibody recognition of BGP. Specific enzymatic cleavage of BGP with tryspin produces three peptides (1–19, 20–43, and 45–49), none of which is antigenic. Thus, the antigenic site may involve either of the pairs of basic residues at sequence positions 19 and 20 or 43 and 44. Because the 1–40 peptide derived from a carboxypeptidase Y digestion of BGP is not antigenic, the COOH-terminal region of BGP is required for antigenicity.

Detection of BGP in Blood Plasma.

Both calf and human plasma displace labeled calf BGP from antibody. The results of several experiments demonstrate that this effect is due to the presence of the BGP in plasma. First, dose dilution curves for human and calf plasma paralleled the radioimmunoassay standard curve. Second, up to 0.1 ml of rat and rabbit plasma failed to displace any labeled calf BGP from antibody, a result that is consistent with the absence of antibody cross-reactivity with purified BGP from these species. Finally, experiments in which purified calf or human BGP was added to the respective plasma samples demonstrated that plasma does not interfere with the quantitative detection of the added BGP by radioimmunoassays.

The form of BGP found in plasma is probably the same as the intact 49-residue protein found in bone. The gel filtration of fetal calf and human plasma on Sephadex G-100 demonstrates that over 90% of the antigenic material elutes in the exact position found for pure calf or human BGP on the same filtration column. The small amount of higher molecular weight immunogen was completely dissociated into BGP by incubation with 6 M guanidine.HCl for 1 hr at 25° C. prior to a second filtration. Thus, plasma BGP is not a proteolytic degradation product of bone BGP. Further indication that plasma BGP is not degraded is the fact that it is antigenic, because tryptic, chymotryptic, or carboxypeptidase digestion destroys antigenicity. Lastly, because BaSO$_4$ removes immunoreactive BGP from plasma, the plasma protein probably contains the region of BGP with the three γ-carboxyglutamate residues that are involved in mineral binding.

Stability of Plasma BGP.

The stability of BGP in plasma was investigated in order to facilitate clinical studies of BGP levels in human plasma samples. In a study of 30 human plasma samples, BGP levels were not affected by four freeze-thaw cycles or by lyophilization followed by reconstitution with either water or radioimmunoassay diluent. The level of BGP in five human plasma samples stored at $-20°$ C. remained constant over a period of 14 months, and BGP levels in 10 human plasma samples were unchanged after 24 hr at 25° C. and after 72 hr at 4° C. No differences in BGP levels could be detected between heparinized plasma and serum samples obtained at the same time from 30 normal individuals.

However, serum BGP levels fell 19% after 8 hr at 25° C., indicating that BGP may be less stable in serum than in plasma.

BGP Levels in Human and Bovine Plasma.

The human plasma levels of BGP were determined by radioimmunoassay of heparinized plasma from 30 normal individuals ranging in age from 18 to 82 years. The average BGP level found in plasma is 4.5±(SD) 2 ng per ml (Table I). The BGP level was also determined in fetal calf serum and in serum obtained from 5-year-old cows. As can be seen in Table I, the BGP level is high in fetal calf serum and is lower in calf and adult cow sera. The elevated BGP level in plasma from immature animals may be due to the increased level of bone metabolism in animals with net bone growth.

TABLE I

BGP Level in Normal Plasma

| Type of sample | Number of samples | BGP, ng per ml |
|---|---|---|
| Human plasma | 30 | 4.5 ± 2 |
| Fetal calf serum | 5 | 200 ± 20 |
| Calf serum | 5 | 50 ± 6 |
| Adult cow serum | 5 | 26 ± 3 |

BGP levels were determined by radioimmunoassay of plasma from normal humans and of sera from fetal calves, 6-month-old calves, and 5-year-old cows. The level of BGP in human plasma is given in nanograms of calf BGP. Values are means ±SD.

Employing the reagents and techniques described above, clinical studies were formed with human subjects.

METHODS

A total of 109 normal subjects and 120 patients with various bone disorders were studied after informed consent was obtained. With the exception of the patients with chronic renal disease, all had normal renal function. For all subjects and patients, a heparinized plasma sample was collected for biochemical determinations from an overnight fast. The normal adults had no evidence of calcium or skeletal abnormalities by routine history, physical, and biochemical evaluation. The patients with Paget's disease each had polyostotic involvement; a history, physical, biochemical evaluation; and xray and/or bone-scan findings diagnostic of this disorder. The patients with bone metastases all had biopsy-proven cancer (two adenocarcinomas of the lung, two small cell carcinomas of the lung, one adenocarcinoma of the breast) and metastases demonstrated by x-ray. Primary hyperparathyroidism was established by surgery, and idiopathic hypoparathyroidism, by a consistent clinical presentation along with hypocalcemia, hyperphosphatemia, and undetectable parathyroid hormone. Liver disease was due to excess alcohol consumption and characterized by elevated serum aspartate aminotransferase, serum alanine aminotransferase, alkaline, phosphatase, and bilirubin. Osteopenia was diagnosed by skeletal x-rays including the presence of vertebral crush fractures and normal calcium and phosphorus.

Alkaline phosphatase was measured spectrophotometrically with p-nitrophenylphosphate substrate according to the manufacturer's (Sigma Chemical Co., St. Louis, Mo.) directions. The normal range was <70 I-U/L. Calcium was determined by atomic absorption spectrophotometry. Gel filtration of plasma samples was performed as previously described; experiments with BGP purified from human bone demonstrate that calf and human BGP coelute in these procedures (Price and Nishimoto (1980) PNAS USA 77, 2234–2238).

RESULTS

Several studies were undertaken to verify that the tracer displacement from antibody produced by plasma from humans is the result of the presence of BGP in plasma. The reactions in the assay of the bovine BGP standard and that of plasma from patients with elevated levels of BGP were found to be indistinguishable. The 50-fold elevated BGP level in plasma from an individual with Paget's disease of bone coelutes with pure BGP on Sephadex G-100 gel filtration. The small level of higher molecular weight immunogen is completely dissociated into BGP by incubation in 6 M guanidine HCl for 1 h at 25° C. before a second filtration. These results indicate that the elevated BGP level in plasma from patients with bone disease is, like BGP in normal bovine, human and rat plasma, probably identical to the 49-residue BGP found in bone.

TABLE II

Relationships Between BGP and AP in Human Blood

|  | BGP ng/ml | AP IU/liter | r | P |
|---|---|---|---|---|
| Normal adults (n = 109) | 6.78(0.20) | 26.7(1.3) | 0.10 | NS |
| Males (n = 47) | 7.89(0.32) | 28.1(2.1) | 0.40 | <0.005 |
| Females (n = 62) | 4.85(0.36) | 25.2(1.8) | −0.17 | NS |
| Paget's disease (n = 13) | 39.2(16)* | 587(181)* | 0.66 | <0.025 |
| Bone metastases (n = 5)+ | 15.8(2.6)* | 132(26)* | 0.93 | <0.05 |
| Hyperparathyroidism |  |  |  |  |
| Primary (n = 11) | 16.5(1.7)* | 64(6.8)* | 0.16 | NS |
| Secondary (n = 38)§ | 47.3(6.1)* | 56(8.5)* | 0.64 | <0.005 |
| Hypoparathyroidism (n = 3) | 2.40(0.92)* | — | — | — |
| Liver disease (n = 11) | 5.77(1.0) | 170(41)* | 0.10 | NS |
| Osteopenia (n = 20) | 9.05(1.8)* | 48(4.6)* | 0.64 | <0.01 |

Except as indicated and in osteopenic group, all subjects are male. Results are mean ± SE.
*Significantly (P < 0.05–0.0005) different from normal controls.
+ Squamous cell carcinoma of the lung (2), adenocarcinoma of the colon (2) and of the breast (2).
§Chronic renal disease on hemodialysis.

Table II summarizes the comparison between BGP and alkaline phosphatase (AP) measurements in normal subjects and in patients with a variety of primary and secondary bone diseases. The patients with bone diseases characterized by increased bone resorption, and increased bone formation in some instances, had increased concentrations of both BGP and AP and were higher in males than in females, but only BGP was significantly ($P<0.01$) so.

TABLE III

Significances and Correlations among BGP, AP, and Age in 109 Normal Subjects

|  | Males (n = 47) | | Females (n = 62) | | Both (n = 109) | |
|---|---|---|---|---|---|---|
|  | r | p | r | p | r | p |
| BGP vs. AP | 0.40 | <0.005 | −0.17 | NS | 0.10 | NS |
| BGP vs. age | 0.10 | NS | −0.44 | <0.005 | −0.24 | <0.005 |
| AP vs. age | 0.24 | NS | 0.30 | <0.005 | 0.23 | <0.01 |

Table III summarizes the relationship among BGP, AP, and age in the normal subjects. For the females, there was a significant ($P<0.005$) negative correlation ($r=0.44$) between BGP and age; and a positive correlation (r=0.30) between AP and age. BGP and AP were significantly (P<0.005) correlated in males only. Both the BGP and AP in the male patients with Paget's disease were among the highest values detected and their levels were generally correlated.

The females with osteopenia (mean age 60 yr) had a mean concentration of BGP that was significantly greater than BGP in normal females (mean age 44 yr) (Table II). However, this group of patients also had concentrations of AP that were generally elevated. It is thus likely that the osteopenic group was heterogenous, and contained females with both osteomalacia and osteoporosis, because AP is not generally considered to be elevated in the latter.

The patients with bone metastases had increased levels of both BGP and AP, and the two were significantly (P<0.05) correlated (r=0.93). Positive correlations between calcium and BGP (r=0.54) and AP (r=0.8) did not achieve significance, perhaps because of the small number (n=5) of patients. In the 11 males with primary hyperparathyriodism, BGP was clearly elevated above normal range for this measurement. As indicated in Table II, however, the mean of AP of the patients was significantly greater than the mean for the normal males. Although three males with idiopathic hypoparathyriodism seemed to have decreased BGP, the number of patients was too small to be conclusive.

It is evident from the above results, that the subject compositions and assay provide for a sensitive and efficient measurement of BGP in physiological fluids and the assay can be used by itself or in conjunction with other assays for the diagnosis of bone related diseases. The use of other than human BGP as a reagent is of great value in view of the difficulty in obtaining or synthesizing BGP from human sources. Thus, large amounts of the BGP for preparation of reagent is readily available. Furthermore, the nonhuman BGP which cross-reacts with human BGP offers a convenient immunogen for production of antibodies which allow for competition between the human BGP and the cross-reacting BGP in a sensitive assay.

Although the foregoing invention has been described in some detail by way of illustration and example for purposes of clarity of understanding, it will be obvious that certain changes and modifications may be practiced within the scope of the appended claims.

We claim:

1. A method for determining vitamin K-dependent bone protein (BGP) in a sample suspected of containing said BGP, said method comprising:
   combining in an aqueous buffered assay medium said sample derived from a human, labeled cross-reacting BGP, wherein said label provides a detectable signal, and antibodies to BGP; and
   determining the amount of labeled BGP either bound or unbound to said antibodies as a measure of human BGP in said sample.

2. A method according to claim 1, wherein said label is a radionuclide.

3. A method according to claim 2, wherein said radionuclide is $^{125}I$.

4. A method according to any of claims 1, 2 or 3, wherein said cross-reacting BGP is bovine BGP.

5. A method according to claim 4, wherein said bovine BGP is calf BGP.

6. A method according to claim 1, wherein said labeled BGP is a fragment of said BGP of at least about 20 amino acids counting from the carboxyl terminus.

7. A method according to claim 1, wherein said antibodies to BGP are produced by immunization of a host with non-human cross-reacting BGP.

8. Antibodies produced in a lagomorpha or rodentia host to bovine BGP.

9. Antibodies according to claim 8, wherein said bovine BGP is calf BGP.

10. Calf BGP labeled with a label capable of providing a detectable signal in an immunoassay.

11. Labeled BGP according to claim 10, wherein said label is a radionuclide.

12. Labeled BGP according to claim 11, wherein said radionuclide is $^{125}I$.

13. Labeled BGP according to claim 10, wherein said label is a fluorescer.

14. Labeled BGP according to claim 10, wherein said label is an enzyme.

* * * * *